(12) United States Patent
Dodo et al.

(10) Patent No.: US 9,850,498 B2
(45) Date of Patent: Dec. 26, 2017

(54) EXPRESSION CASSETTE

(71) Applicant: TAKARA BIO INC., Shiga (JP)

(72) Inventors: Katsuyuki Dodo, Kusatsu (JP);
Takahisa Tsukihara, Uji (JP); Mayumi Shimomura, Kyoto (JP); Koichi Inoue, Otsu (JP); Hideto Chono, Moriyama (JP); Junichi Mineno, Uji (JP); Masanari Kitagawa, Yasu (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 14/649,317

(22) PCT Filed: Dec. 10, 2013

(86) PCT No.: PCT/JP2013/083116
§ 371 (c)(1),
(2) Date: Jun. 3, 2015

(87) PCT Pub. No.: WO2014/092094
PCT Pub. Date: Jun. 19, 2014

(65) Prior Publication Data
US 2015/0329872 A1 Nov. 19, 2015

(30) Foreign Application Priority Data

Dec. 11, 2012 (JP) .................. 2012-269902

(51) Int. Cl.
| C12P 21/02 | (2006.01) |
| C12N 15/63 | (2006.01) |
| C12N 15/85 | (2006.01) |
| C07H 21/00 | (2006.01) |
| C07H 21/04 | (2006.01) |
| C12N 15/09 | (2006.01) |
| C12N 15/113 | (2010.01) |

(52) U.S. Cl.
CPC ............ *C12N 15/85* (2013.01); *C12N 15/63* (2013.01); *C12N 2740/16311* (2013.01)

(58) Field of Classification Search
None
See application file for complete search history.

(56) References Cited

FOREIGN PATENT DOCUMENTS

| JP | 2004-509642 | 4/2004 |
| WO | 02/027005 | 4/2002 |

OTHER PUBLICATIONS

International Search Report dated Mar. 4, 2014 in International Application No. PCT/JP2013/083116.
International Preliminary Report on Patentability dated Jun. 16, 2015 in International Application No. PCT/JP2013/083116.
Myung-Sam Cho et al., "An oriP expression vector containing the HIV-1 Tat/TAR transactivation axis produces high levels of protein expression in mammalian cells", Cytotechnology, 2001, 37, pp. 23-30.
M. Reza Sadaie, et al., "Towards Developing HIV-2 Lentivirus-Based Retroviral Vectors for Gene Therapy: Dual Gene Expression in the Context of HIV-2 LTR and Tat", Journal of Medical Virology, 1998, 54, p. 118-128.
D. Robinson, et al., "*Retroviral vector with a CMV-IE/HIV-TAR hybrid LTR gives high basal expression levels and is up-regulated by HIV-1 Tat*", Gene Therapy, 2 (4), 1995, p. 369-278.
Dominique Dorin et al., "The TAR RNA-binding Protein, TRBP, Stimulates the Expression of TAR-containing RNAs in Vitro and in Vivo Independently of Its Ability to Inhibit the dsRNA-dependent Kinase PKR*", The Journal of Biological Chemistry, 2003, vol. 278, No. 7, p. 4440-4448.
Extended European Search Report dated Jul. 19, 2016, in corresponding European Application No. 13862559.5.
Negrini, M. et al., "High Expression of Exogenous cDNAs Directed by HIV-1 Long Terminal Repeat in Human Cells Constitutively Producing HIV-1 tat and Adenovirus E1A/E1B", BioTechniques, Informa Healthcare, vol. 10, No. 3, 1991, pp. 344-353.
Mautino, Mario R., "Lentiviral Vectors for Gene Therapy of HIV-1 Infection", Current Gene Therapy, vol. 2, No. 1, 2002, pp. 23-43.
Kitagawa I., Product Manual for pHEK293 Ultra Expression Vector I and pHEK293 Ultra Expression Vector II, 2013, XP055284829, pp. 1-11, retrieved from http://www.takara.com.cn/DownLoad/3390,3392.pdf.
Chinese Office Action dated Sep. 2, 2016, issued in corresponding Chinese Patent Application No. 201380072638.X (with English Translation).
Chinese Office Action dated Apr. 20, 2017 issued in corresponding Chinese Patent Application No. 201380072638.X (with English translation).
Office Action dated Sep. 26, 2017 in Japanese Application No. 2014-552056, with English Translation.

*Primary Examiner* — Nancy J Leith
(74) *Attorney, Agent, or Firm* — Wenderoth, Lind & Ponack, L.L.P.

(57) ABSTRACT

The present invention provides an expression cassette comprising (1) an expression regulatory region having a sequence corresponding to a transcriptional activator-binding region and (2) a nucleic acid encoding a transcriptional activator which is capable of binding to the expression regulatory region, wherein the nucleic acid is operably linked to the expression regulatory region; a method for expressing a target product in a mammalian cell, a method for producing a cell expressing a target product, and a method for producing a target product in a mammalian cell using the expression cassette; and a kit comprising the expression cassette.

8 Claims, 2 Drawing Sheets

[Fig. 1]

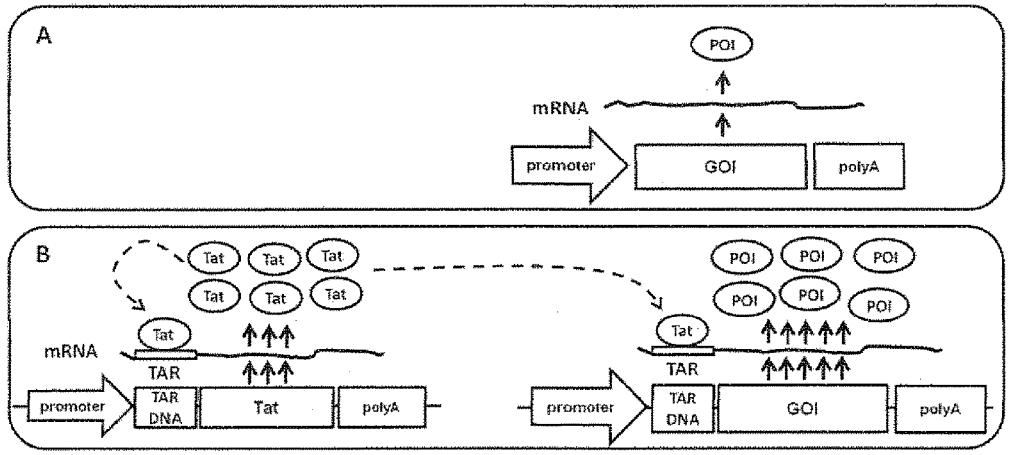

A: Schematic drawing of a general target product-expression cassette.
B: Schematic drawing of a method for expressing according to the present invention using a transcriptional activator-expression cassette expressing Tat and a target product-expression cassette comprising an expression regulatory region having a sequence corresponding to TAR.

GOI: Gene of Interest
POI: Protein of Interest

[Fig. 2]

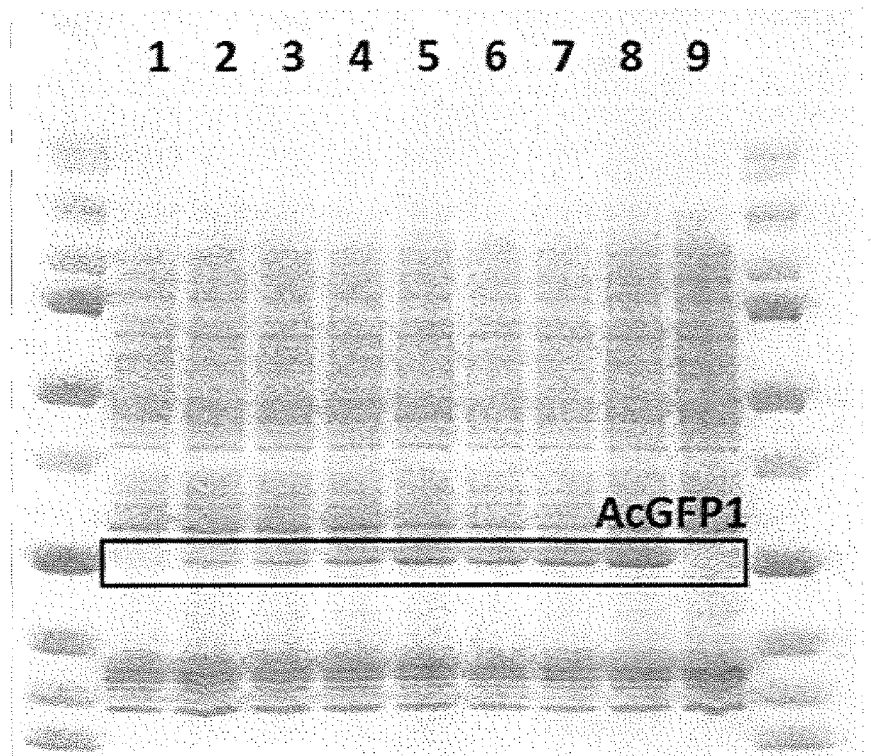

[Fig. 3]
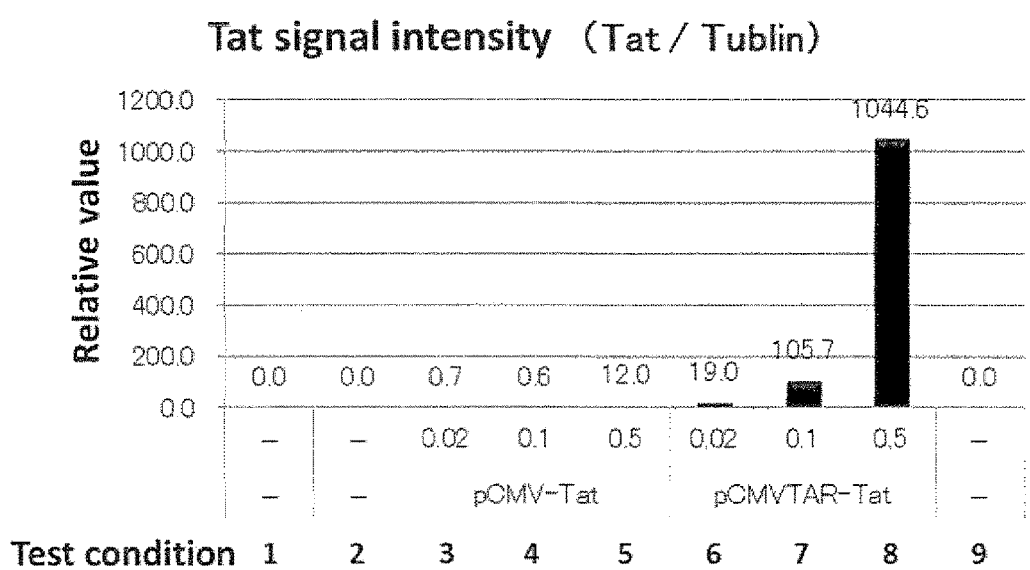

EXPRESSION CASSETTE

TECHNICAL FIELD

The present invention relates to an expression cassette useful for producing genetically engineered products, and a use of the expression cassette.

BACKGROUND ART

For the production of a polypeptide such as a recombinant protein, methods for introducing a nucleic acid encoding the polypeptide into prokaryotes, yeast, insect cells, protozoa, mammalian cells, or the like by using a plasmid vector or a virus vector, and transcribing and translating the nucleic acid by using a protein production system in the host cell are used. Especially, a method using mammalian cells is suitable for studies or clinical applications in the fields of not only protein engineering and molecular genetics but also immunoengineering, gene therapy, and pharmaceutical product production because the post-translational modification is the same as that of human and a protein derived from a mammal can be correctly folded, etc.

However, in the method for producing a recombinant protein using a mammalian cell, the product is often insufficiently obtained compared with the methods using prokaryotes or yeast. As techniques for solving this problem, for example, the technique in which an episomal maintenance system and a strong promoter/enhancer are added to a protein expression system having a transactivation system in a recombinant protein expression system using a human cell (Patent Literature 1), and the technique for improving an expression of a protein under the control of an expression regulatory region having CMV promoter and trans-activation-responsive region (hereinafter, referred to as TAR) by a binding action of human TRBP that is a binding factor of TAR of human immunodeficiency virus type 1 (hereinafter, referred to as HIV-1) to TAR (Non-Patent Literature 1) are known.

CITATION LIST

Patent Literature

Patent Literature 1: WO2002/027005

Non-Patent Literature

Non-Patent Literature 1: The Journal of Biological Chemistry, Vol. 278, pp. 4440-4448 (2003)

SUMMARY OF INVENTION

Problems to be Solved by the Invention

An objective of the present invention is to provide a method for highly-expressing a target product etc. without complicated operations.

Solutions to the Problems

The inventors intently studied methods for improving the expression amount of a target product. As a result, the inventors constructed an expression cassette in which a nucleic acid encoding a transcriptional activator which binds to a transcriptional activator-binding region is operably linked to an expression regulatory region having a sequence corresponding to the transcriptional activator-binding region. Then, the inventors found that the expression amount of a target product was improved by combining an introduction of said cassette as a first expression cassette (hereinafter, also referred to as "transcriptional activator-expression cassette") into mammalian cells with an introduction of a second expression cassette in which a nucleic acid sequence for expressing the target product is operably linked to an expression regulatory region having a sequence corresponding to the same transcriptional activator-binding region as that of the transcriptional activator-expression cassette (hereinafter, also referred to as "target product-expression cassette") into the mammalian cells, and thus, the present invention was completed (FIG. 1). According to the present invention, not only a production of a polypeptide but also a production of RNA or virus vector is achieved at a high efficiency.

The present invention is outlined as follows. The present invention relates to:

[1] An expression cassette comprising the following (1) and (2):
  (1) an expression regulatory region having a sequence corresponding to a transcriptional activator-binding region; and
  (2) a nucleic acid encoding a transcriptional activator which is capable of binding to the expression regulatory region, wherein the nucleic acid is operably linked to the expression regulatory region;

[2] The expression cassette of [1], wherein a nucleic acid for expressing a target product is further operably linked to the expression regulatory region having the sequence corresponding to the transcriptional activator-binding region;

[3] The expression cassette of [1] or [2], wherein the transcriptional activator is Tat of immunodeficiency virus or a functionally homologous variant thereof;

[4] The expression cassette of any one of [1]-[3], wherein the transcriptional activator-binding region is a trans-activation-responsive region of immunodeficiency virus or a functionally homologous sequence thereof;

[5] A method for expressing a target product in a mammalian cell comprising the following steps (a) and (b):
  (a) introducing into a cell a first expression cassette comprising a first expression regulatory region and a nucleic acid encoding a transcriptional activator that is operably linked to the first expression regulatory region, and a second expression cassette comprising a second expression regulatory region and a nucleic acid for expressing the target product that is operably linked to the second expression regulatory region; and
  (b) culturing the cell obtained in the step (a), wherein the first expression regulatory region and the second expression regulatory region have a sequence corresponding to a transcriptional activator-binding region to which the transcriptional activator encoded in the first expression cassette binds;

[6] A method for expressing a target product in a mammalian cell comprising the following steps (a) and (b):
  (a) introducing into a cell the expression cassette of [1] wherein a nucleic acid for expressing the target product is further operably linked to the expression regulatory region having the sequence corresponding to the transcriptional activator-binding region; and
  (b) culturing the cell obtained in the step (a);

[7] The method of [5] or [6], wherein the transcriptional activator is Tat of immunodeficiency virus or a functionally homologous variant thereof;

[8] The method of any one of [5]-[7], wherein the transcriptional activator-binding region is a trans-activation-responsive region of immunodeficiency virus or a functionally homologous sequence thereof;

[9] A method for producing a cell expressing a target product, comprising
a step of introducing into a mammalian cell a first expression cassette comprising a first expression regulatory region and a nucleic acid encoding a transcriptional activator that is operably linked to the first expression regulatory region, and a second expression cassette comprising a second expression regulatory region and a nucleic acid for expressing the target product that is operably linked to the second expression regulatory region,
wherein the first expression regulatory region and the second expression regulatory region have a sequence corresponding to a transcriptional activator-binding region to which the transcriptional activator encoded in the first expression cassette binds;

[10] A method for producing a cell expressing a target product, comprising
a step of introducing into a mammalian cell the expression cassette of [1] wherein a nucleic acid for expressing the target product is further operably linked to the expression regulatory region having the sequence corresponding to the transcriptional activator-binding region;

[11] The method of [9] or [10], wherein the transcriptional activator is Tat of immunodeficiency virus or a functionally homologous variant thereof;

[12] The method of any one of [9]-[11], wherein the transcriptional activator-binding region is a trans-activation-responsive region of immunodeficiency virus or a functionally homologous sequence thereof;

[13] A method for producing a target product in a mammalian cell comprising the following steps (a) and (b):
(a) expressing the target product by the method of any one of [5]-[8]; and
(b) obtaining the expressed target product;

[14] A kit comprising the following (1) and (2):
(1) a first expression cassette comprising a first expression regulatory region and a nucleic acid encoding a transcriptional activator that is operably linked to the first expression regulatory region; and
(2) a second expression cassette comprising a second expression regulatory region and a site into which a nucleic acid for expressing a target product is insertable so that the nucleic acid is operably linked to the second expression regulatory region,
wherein the first expression regulatory region and the second expression regulatory region have a sequence corresponding to a transcriptional activator-binding region to which the transcriptional activator encoded in the first expression cassette binds;

[15] The kit of [14], wherein the first expression cassette and the second expression cassette are contained in different nucleic acid constructs, respectively;

[16] The kit of [14], wherein the first expression cassette and the second expression cassette are contained in the same nucleic acid construct;

[17] A kit comprising the expression cassette of [1], wherein the first expression cassette further comprises a site into which a nucleic acid for expressing a target product is insertable so that the nucleic acid is operably linked to the first expression regulatory region;

[18] The kit of any one of [14]-[17], wherein the transcriptional activator is Tat of immunodeficiency virus or a functionally homologous variant thereof; and

[19] The kit of any one of [14]-[18], wherein the transcriptional activator-binding region is a trans-activation-responsive region of immunodeficiency virus or a functionally homologous sequence thereof.

Effects of the Invention

According to the present invention, a transcriptional activator-expression cassette useful for supplying a transcriptional activator in a cell is provided. In addition, provided are a method for expressing a target product and a method for producing a target product as well as a method for producing a cell expressing a target product, using this transcriptional activator-expression cassette and a target product-expression cassette having in a expression regulatory region a sequence corresponding to a transcriptional activator-binding region to which the transcriptional activator binds. Moreover, a kit used in the methods is provided. The present invention is very useful for basic studies or clinical applications in the fields of not only protein engineering and molecular genetics but also immunoengineering, gene therapy, and pharmaceutical production.

BRIEF DESCRIPTION OF DRAWINGS

FIG. 1 shows a concept of the present invention. Fig. A is a schematic drawing of a general target product-expression cassette. Fig. B is a schematic drawing of a method for expressing according to the present invention using a transcriptional activator-expression cassette expressing Tat and a target product-expression cassette comprising an expression regulatory region having a sequence corresponding to TAR.

FIG. 2 shows results of SDS-polyacrylamide gel electrophoresis of the cell lysates prepared in Example 2-(1).

FIG. 3 shows Tat signal intensities under each test condition.

MODE FOR CARRYING OUT THE INVENTION

As used herein, an expression cassette refers to a nucleic acid construct comprising elements necessary to express a target product. Specifically, it refers to a nucleic acid construct comprising an expression regulatory region comprising at least a promoter, and a nucleic acid for expressing the target product that is operably linked to the expression regulatory region.

As used herein, "operably linked" in regard to a nucleic acid for expressing a target product means that the nucleic acid for expressing the target product is located at an appropriate position with respect to an expression regulatory region so that the target product can be expressed. In general, the expression regulatory region is operably located to be positioned in cis with respect to the nucleic acid for expressing the target product. However, it does not need to be directly adjacent to the nucleic acid for expressing the target product. It may also be located to a plurality of nucleic acids for expressing target products that is located via IRES (Internal Ribosome entry site) sequence, a 2A peptide coding sequence, or the like. When a plurality of nucleic acids for expressing target products is located, a plurality of nucleic acids expressing the same target product may be located, or a plurality of nucleic acids for expressing different target products may be located.

As used herein, an expression regulatory region refers to a region which controls the expression of a target product in an expression cassette. Specifically, it refers to a region comprising a promoter. The expression regulatory region may further comprise various regulatory sequences involved in a transcriptional regulation. Examples of the promoter in the present invention include, but not particularly limited to, any promoters that functions in a mammalian cell, and preferred examples include: a constitutive expression promoter such as CMV promoter, SV40 promoter, EF-1α promoter, CAG promoter, and PGK promoter; U3 promoter; U6 promoter; H1 promoter; and the like. In addition to these promoters, a known inducible promoter, a tissue- or organ-specific promoter, a time-specific promoter, or variant sequences having functional equivalence thereto, or the like may be used in the present invention. Preferred examples of the promoter in the present invention include promoters that are derived from an origin different from that of the transcriptional activator-binding region described below, and in particular, preferred examples include CMV promoter having high transcriptional efficiency.

In the expression regulatory region in the expression cassette of the present invention, a sequence corresponding to a transcriptional activator-binding region is located around a promoter or in an untranslated region on the downstream of a transcription initiation site for the purpose of increasing transcriptional efficiency. Examples of the sequence corresponding to the transcriptional activator-binding region include a base sequence of the transcriptional activator-binding region that is RNA, or DNA sequence corresponding to the sequence. A transcriptional activator-binding region is a sequence which increases transcriptional efficiency of a gene comprised in the expression cassette by an interaction (association/dissociation) with a specific transcriptional activator. As necessary, the sequence corresponding to the transcriptional activator-binding region may be used at a plurality of positions or as a repeat sequence in an expression vector. The interaction occurs between RNA transcribed from the transcriptional activator-binding region and the transcriptional activator. Examples of the transcriptional activator-binding region include TAR which exists in 5'-terminal repeat sequence (LTR) of immunodeficiency virus such as HIV-1, HIV-2, and SIV. TAR is a region which exists in LTR of immunodeficiency virus and forms a higher-order structure, and binding of a transcriptional activator Tat (Trans Activator) to the region promotes a transcription of immunodeficiency virus RNA. Accordingly, in an aspect of the present invention, the above-mentioned expression regulatory region is constructed so that the transcriptional activator-binding region is formed on mRNA generated by the transcription. Preferred examples of the sequence corresponding to the transcriptional activator-binding region in the present invention particularly include a nucleic acid comprising a sequence corresponding to TAR derived from HIV-1 that is shown in SEQ ID NO: 2 in the sequence listing. In addition, a base sequence of TAR used in the present invention may be a base sequence derived from wild-type, or may be a functionally homologous base sequence thereof. The functionally homologous base sequence is not particularly limited as long as it has a binding ability to Tat, and examples include sequences having 95% or more, preferably 98% or more homology to the base sequence of SEQ ID NO: 2 in the sequence listing.

As used herein, a transcriptional activator refers to a factor which is a protein having an RNA-binding ability, binds to RNA either singly or by forming a dimer or a complex, and acts so as to further increase transcriptional efficiency dependent on a promoter. Examples of the transcriptional activator include Tat which is a transcriptional activator of immunodeficiency virus such as HIV-1, HIV-2, and SIV, and TRBP which is a transactivator derived from human. Preferred examples of the transcriptional activator in the present invention include Tat which is a transcriptional activator of HIV-1 and is shown in SEQ ID NO: 1 in the sequence listing. Tat is a factor which promotes transcription of RNA of immunodeficiency virus by binding to TAR comprised in LTR of the immunodeficiency virus. Therefore, a transcription from an expression regulatory region having TAR downstream from a transcription initiation site is promoted by Tat. In addition, Tat used in the present invention may be wild-type or a variant thereof. The variant is not particularly limited as long as it has a binding ability to TAR, and examples include variants consisting of an amino acid sequence having 95% or more, preferably 98% or more identity to the amino acid sequence encoded by the base sequence of SEQ ID NO: 1 in the sequence listing.

The transcriptional activator-expression cassette provided by the present invention may be created by operably linking a nucleic acid encoding a transcriptional activator which binds to a transcriptional activator-binding region to an expression regulatory region having a promoter and a sequence corresponding to the transcriptional activator-binding region, preferably by linking it so that the sequence corresponding to the transcriptional activator-binding region is located between a transcription initiation site and a translation initiation site. More preferably, it may be created by linking the sequence corresponding to the transcriptional activator-binding region and the nucleic acid encoding the transcriptional activator via a DNA fragment of, for example 500 bp or less, preferably, 300 bp or less, more preferably, 100 bp or less. The transcriptional activator-expression cassette created in such a way is characterized in that it has a positive feedback effect of promoting a further expression of the transcriptional activator by the interaction of the expressed transcriptional activator with the transcriptional activator-binding region on the mRNA transcribed from the same cassette.

The expression cassette for a target product in the present invention may be created by operably linking a nucleic acid for expressing the target product to an expression regulatory region having a promoter and a sequence corresponding to a transcriptional activator-binding region. This nucleic acid may be of natural origin or artificially synthesized as long as the desired product is obtained. In addition, a base sequence of this nucleic acid may be a native base sequence or may be a base sequence in which one or more bases are substituted, deleted, and/or inserted in the native base sequence. The above-mentioned transcriptional activator-binding region is a sequence to which a transcriptional activator expressed from a transcriptional activator-expression cassette used together binds. Examples of the target product include, but not particularly limited to, for example, polypeptides such as fluorescence proteins, various growth factors, enzymes, and antibodies. In addition, the target product do not necessarily need to be a product produced via a translation, and it may be a nucleic acid which is a transcript, such as rRNA, tRNA, small nuclear RNA, shRNA, siRNA, and antisense RNA.

The method for expressing according to the present invention is achieved by introducing into a cell the transcriptional activator-expression cassette and the target product-expression cassette and culturing the resultant cell. The expression regulatory regions of the two types of cassettes, i.e., the transcriptional activator-expression cassette and the target product-expression cassette, in the method for expressing according to present invention have the sequence corresponding to the transcriptional activator-binding region to which the transcriptional activator expressed from the transcriptional activator-expression cassette binds, respectively.

The method for producing a cell expressing a target product according to the present invention is achieved by introducing into a cell the transcriptional activator-expression cassette and the target product-expression cassette.

Two types of cassettes, i.e., the transcriptional activator-expression cassette and the target product-expression cassette in the present invention may be contained in different nucleic acid constructs, respectively, or may be contained in the same nucleic acid construct. If the cassettes are contained in the same nucleic acid construct, the first expression regulatory region and the second expression regulatory region may be covered with a single expression regulatory region. Namely, both the nucleic acid encoding the transcriptional activator and the nucleic acid for expressing the target product may be operably linked to the single expression regulatory region. In this case, IRES sequence or a sequence encoding 2A peptide may be inserted, for example, between the nucleic acid encoding the transcriptional activator and the nucleic acid sequence for expressing the target product. If IRES sequence or a sequence encoding 2A peptide is inserted, the nucleic acid sequence for expressing the target product may be located on the upstream of these sequences and the nucleic acid sequence encoding the transcriptional activator may be located downstream, and vice versa.

In a preferred aspect of the present invention, the expression cassettes are contained in a plasmid vector or a virus vector and used. Preferred examples of the plasmid vector include, but not particularly limited to, for example, pBApo-CMV DNA, and pIRES Bicistronic Expression Vector (both manufactured by Takara Bio Inc.) that are expression vectors for mammal. In addition, preferred examples of the virus vector include, but not particularly limited to, for example, a retroviral vector, a lentiviral vector, and an adenoviral vector, and a commercial product can be used as each vector. Furthermore, each one type of both expression cassettes may be used, or a plurality of types of the expression cassettes may be used. For example, as described in Example 10 below, a nucleic acid construct comprising two or more different types of target product-expression cassettes may be used in the method for expressing according to the present invention, or a nucleic acid construct comprising an expression cassette of a shRNA library, or a nucleic acid construct comprising an expression cassette of a siRNA library, or the like may be used in the method of the present invention. Moreover, a nucleic acid construct comprising a plurality of one type of the target product-expression cassette may be used in the method of the present invention.

In the method of the present invention, preferred examples of the cell into which the expression cassette is introduced include, but not particularly limited to, a mammalian cell. The mammalian cell is not limited as long as the expression of the target product is achieved by the method of the present invention. For example, examples of the mammalian cell include, an adherent or floating HEK293 cell or 293T cell, 293F cell or 293FT cell (all manufactured by Life Technologies), G3T-hi cell (manufactured by TAKARA Bio Inc.: WO06/035829), HeLa cell (ATCC CCL-2), MOLT-4 cell (ATCC CRL-1582), and PER.C6 (registered trademark) cell (ATCC CCL-2). Examples of a primate cell other than a human cell include, for example, COS-1 cell (ATCC CRL-1650) and COS-7 cell (ATCC CRL-1651), and examples of a rodent cell include, for example, CHO cell (ATCC CCL-61) and HePaI-6 cell (ATCC CRL-1830).

In the present invention, examples of a method for introducing the expression cassette into a cell include, but not particularly limited to, known introduction methods in which the introduced nucleic acid construct comprising the expression cassette are maintained transiently or stably in the cell. For example, examples of the method for introducing a plasmid vector include a calcium phosphate method, a lipofection method, a DEAE-dextran method, a polyethyleneimine method, and an electroporation method. For the introduction, commercially available reagents such as TransIT (registered trademark)-293 Reagent (manufactured by Mirus Bio LLC), Lipofectamine 2000 Reagent (manufactured by Life Technologies), FuGene (registered trademark) (manufactured by Promega Corporation) may be used. In addition, a cell having the introduced nucleic acid construct on its chromosome may be obtained by the method for introducing the nucleic acid construct into a cell and then selectively proliferating a cell incorporating the introduced nucleic acid construct into its genome. Furthermore, if a virus vector is used, a cell may be infected with the virus vector by an appropriate method depending on the property of the virus vector. It goes without saying that commercially available kits or the like may be used for these nucleic acid introducing methods.

The culture condition in the method for expressing according to the present invention is not particularly limited as long as it achieves a proliferation of the desired cell and an acquisition of the target product. For example, conditions used in the usual cell culture may be performed. For example, examples of the culture condition include a culture at a temperature of 30 to 37° C., with a humidity of 90 to 100% and a $CO_2$ concentration of 3 to 10%.

The method for producing a target product according to the present invention is achieved by using the method for expressing according to the present invention and obtaining the target product. The method for obtaining the target product is not particularly limited, and, for example, the target product may be obtained using techniques known to those skilled in the art from cells and/or culture supernatant. In the method for producing according to the present invention, a target product is not necessarily isolated. Namely, "obtain a target product" in the present invention also means obtaining a culture itself comprising the target product, and obtaining a crude product from the culture (for example, obtaining a culture supernatant). In addition, the target product may be extracted, concentrated, or purified by further using a known method.

The method of the present invention is not limited to aspects in which a single polypeptide or RNA is obtained. For example, a method for producing a virus vector consisting of a plurality of proteins and nucleic acids, such as retroviral vector, is also one aspect of the present invention. Examples of the method for producing the virus vector include a method comprising: introducing into a cell expression cassette(s) for protein(s) necessary for the virus vector production and an expression cassette for a nucleic acid to be encapsulated in the viral particle together with a transcription factor-expression cassette; culturing the resultant cell under a condition suitable for the virus vector production; and obtaining the virus vector produced in the cell and/or culture supernatant.

Furthermore, in the method of the present invention, for example, a polypeptide increasing the transcriptional efficiency of the expression cassette of the present invention may be used. Examples of the polypeptide include, for example, ELL2, AFF4, ENL, AF9, and p-TEFb and transcription elongation factors such as CyclinT1 and cdk9 that compose p-TEFb. In addition, RNA polymerase II may be used. These polypeptides may be expressed in a cell by using a known method.

According to the present invention, a kit comprising the expression cassette of the present invention is also provided. In one aspect, the kit of the present invention is a kit comprising the transcriptional activator-expression cassette. In another aspect, the kit of the present invention is a kit comprising the transcriptional activator-expression cassette mentioned above, and an expression cassette (cassette for expressing a target product) comprising an expression regulatory region having a sequence corresponding to a transcriptional activator-binding region to which this transcriptional activator binds and a site into which a nucleic acid for expressing a target product is insertable so that the nucleic acid is operably linked to the expression regulatory region. For example, examples of aspects of the kit of the present invention include a combination of a vector containing the transcriptional activator-expression cassette and a vector containing the cassette for expressing the target product, and a vector containing both cassettes. In the vector containing both cassettes, the transcriptional activator and the target product may be expressed by a single expression regulatory region. Examples of the vector used in the kit of the present invention include, but not particularly limited to, a plasmid vector and a virus vector. In addition, the kit of the present invention may further include, for example, an instruction, a reagent for introducing a nucleic acid or for cloning, and/or a host cell. When the kit further includes a host cell, the transcriptional activator-expression cassette of the present invention may be pre-introduced into the host cell. The kit of the present invention is particularly useful for carrying out the above-mentioned method of the present invention.

EXAMPLES

Hereinafter, the present invention is more specifically explained by way of Examples. However, the present invention is not limited to the Examples.

Example 1: Constructions of a Transcriptional Activator-Expression Cassette Using Tat and TAR and a Target Product-Expression Cassette (1) Construction of a Transcriptional Activator-Expression Cassette: pCMVTAR-Tat Plasmid A nucleic acid encoding Tat derived from the HIV-1 strain NL4-3 (SEQ ID NO: 1) was inserted into a multiple cloning site of pBApo-CMV DNA (manufactured by Takara Bio Inc.) to construct pCMV-Tat plasmid. pBApo-CMV DNA is a gene expression plasmid for a mammalian cell that comprises a promoter derived from cytomegalovirus (CMV IE promoter) and poly A signal of herpes simplex virus thymidine kinase. Subsequently, a nucleic acid comprising a sequence corresponding to TAR derived from LTR of HIV-1 (SEQ ID NO: 3) were obtained by using PCR, and this nucleic acid was inserted between the CMV promoter and the nucleic acid encoding Tat in the pCMV-Tat plasmid to create pCMVTAR-Tat plasmid. pCMVTAR-Tat plasmid is characterized in that it has a positive feedback effect of further promoting Tat-expression by binding of Tat expressed from the plasmid to TAR on the same plasmid.

(2) Construction of a Target Product-Expression Cassette: pCMVTAR-AcGFP1 Plasmid A nucleic acid shown in SEQ ID NO: 3 were inserted into a multiple cloning site of pBApo-CMV DNA to construct pCMV-TAR plasmid. Then, a nucleic acid encoding a fluorescence protein AcGFP1 was inserted into a multiple cloning site located downstream of TAR on the pCMV-TAR plasmid to construct pCMVTAR-AcGFP1 plasmid. In addition, as a control, a nucleic acid encoding AcGFP1 was inserted into a multiple cloning site of pBApo-CMV DNA to construct pCMV-AcGFP1 plasmid.

Example 2: Enhancement of AcGFP1 Expression by Tat-Expression (1) Evaluation by AcGFP1 Fluorescence Intensity Adherent 293T cells were seeded in a surface-treated 12-well plate (manufactured by Becton, Dickinson and Company) at $2.5 \times 10^5$ cells/1 mL per well and cultured in a $CO_2$ incubator (at 37° C., with a humidity of 95% and $CO_2$ concentration of 5%). As a medium, DMEM medium (manufactured by Sigma-Aldrich Co. LLC) to which fetal bovine serum (FBS, manufactured by Life Technologies) was added so as to be 10% was used. After 24-hours incubation, the plasmids were introduced into the cultured cells. The introduction was performed under 9 different test conditions in which the type and the amount (per 1 well) of the used plasmids were different. Table 1 shows the type and the amount of the plasmids used under each test condition. In addition, the introduction of the plasmids was performed with TransIT-293 according to the protocol attached to the kit.

TABLE 1

| | AcGFP1 expression plasmid | | Tat expression plasmid | |
|---|---|---|---|---|
| Experiment | Plasmid Name | Amount of plasmid (µg) | Plasmid Name | Amount of plasmid (µg) |
| 1 | pCMV-AcGFP1 | 1.0 | — | — |
| 2 | pCMVTAR-AcGFP1 | 1.0 | — | — |
| 3 | pCMVTAR-AcGFP1 | 1.0 | pCMV-Tat | 0.008 |
| 4 | pCMVTAR-AcGFP1 | 1.0 | pCMV-Tat | 0.04 |
| 5 | pCMVTAR-AcGFP1 | 1.0 | pCMV-Tat | 0.2 |
| 6 | pCMVTAR-AcGFP1 | 1.0 | pCMVTAR-Tat | 0.008 |
| 7 | pCMVTAR-AcGFP1 | 1.0 | pCMVTAR-Tat | 0.04 |
| 8 | pCMVTAR-AcGFP1 | 1.0 | pCMVTAR-Tat | 0.2 |
| 9 | — | — | — | — |

The cells after the introduction were cultured in a $CO_2$ incubator for two days. The next day of the introduction, the medium in each well was exchanged with DMEM medium added with 10% FBS, and after two days of incubation, the cells were harvested. After $5 \times 10^5$ of cells of the harvested cells were washed with PBS (manufactured by Life Technologies), 50 µL of 1×SDS sample buffer (50 mM Tris-HCl pH 6.8, 10% glycerol, 2% sodium dodecyl sulfate (SDS), 0.005% bromophenol blue, 100 mM dithiothreitol) was added thereto, and a heat-treatment at 95° C. for five minutes was performed to use the resultant as cell lysates. The remaining cells were subjected to a flow cytometry to measure fluorescence by AcGFP1 expressed in the cell.

Table 2 shows the mean fluorescence intensities of the cells in which the fluorescence was observed.

TABLE 2

| Test condition | Mean fluorescence intensity |
| --- | --- |
| 1 | 1,051 |
| 2 | 3,371 |
| 3 | 4,401 |
| 4 | 5,364 |
| 5 | 8,235 |
| 6 | 7,452 |
| 7 | 10,181 |
| 8 | 11,262 |
| 9 | 0 |

As a result, the AcGFP1 fluorescence intensity was low under the condition in which the Tat expression plasmid was not used (test condition 1). On the other hand, the AcGFP1 fluorescence intensity was increased in correlation with the used amount of each Tat expression plasmid under the conditions in which the Tat expression plasmid was used (test conditions 3-8). Furthermore, fluorescence intensity was markedly increased under the conditions in which pCMVTAR-Tat plasmid having the transcriptional activator-expression cassette of the present invention was used as the Tat expression plasmid (test conditions 6-8). In particular, the fluorescence intensity of ten times higher than that under the test condition 1 was obtained under the condition in which 0.2 μg of pCMVTAR-Tat was used (test condition 8). This showed that AcGFP1-expression was increased due to the presence of Tat and correlated with Tat expression amount. Moreover, it was shown that Tat expression was increased by a positive feedback effect of pCMVTAR-Tat plasmid, and thereby AcGFP1-expression was markedly enhanced.

(2) Evaluation by SDS-Polyacrylamide Gel Electrophoresis

The cell lysates prepared in Example 2-(1) were applied on a SDS-polyacrylamide gel at $2 \times 10^4$ cells per lane and an electrophoresis was performed. After the electrophoresis, the gel was stained with Coomassie Brilliant Blue. FIG. 2 shows the stained gel image. Then, the stained gel image was captured by a scanner, and signal intensities of bands of AcGFP1 were calculated with the image analysis software LuminoShot (registered trademark) Analyzer 2.0 (manufactured by Takara Bio Inc.). The calculation of the signal intensities was performed as follows. Firstly, the signal intensities of bands of AcGFP1 existing near 25 kDa and bands of proteins derived from 293T cells near 15 kDa of each lane were converted into numerical values. Next, the signal intensities of the bands of AcGFP1 were corrected on the basis of the signal intensities of the bands of proteins derived from 293T cells near 15 kDa. Furthermore, the signal intensity near 25 kDa of the negative control (lane 9) was subtracted from the corrected values of the signal intensities of the bands of AcGFP1, and the obtained values were used as the signal intensities of the bands of AcGFP1. Table 3 shows the results.

TABLE 3

| Test condition | Signal intensity of AcGFP1 band |
| --- | --- |
| 1 | −116,134 |
| 2 | 1,430,844 |
| 3 | 2,692,698 |

TABLE 3-continued

| Test condition | Signal intensity of AcGFP1 band |
| --- | --- |
| 4 | 4,454,222 |
| 5 | 6,233,527 |
| 6 | 6,935,688 |
| 7 | 8,197,886 |
| 8 | 8,531,884 |
| 9 | 0 |

As shown in FIG. 2, no band of AcGFP1 was found under the condition in which the pCMV-AcGFP1 plasmid was used (lane 1). On the other hand, AcGFP1 was found as major bands under the condition in which the Tat expression plasmid was used (lanes 3-8).

In addition, as shown in Table 3, the signal intensity was increased in correlation with the used amount of each Tat expression plasmid under the conditions in which the Tat expression plasmid was used (test conditions 3-8). Furthermore, under the condition in which pCMVTAR-Tat was used (test conditions 6-8), the signal intensity was markedly increased, compared with the conditions in which pCMV-Tat was used (test conditions 3-5). This showed that AcGFP1-expression was increased due to the presence of Tat and correlated with Tat expression amount. Moreover, it was deduced that Tat expression was increased by a positive feedback effect of pCMVTAR-Tat plasmid, and thereby AcGFP1-expression was markedly enhanced.

Example 3: Effect on Tat Protein-Expression Enhancement by pCMVTAR-Tat

Similar to Example 2, the AcGFP1 expression plasmid and the Tat expression plasmid were introduced into adherent 293T cells. In this Example, a surface-treated 6-well plate (manufactured by Becton, Dickinson and Company) was used as a culture carrier and the condition for seeding cells per well was $6 \times 10^5$ cells/2.5 mL. Table 4 shows the type and the amount of the plasmids used for the introduction.

TABLE 4

| Test condi- tion | AcGFP1 expression plasmid | | Tat expression plasmid | |
| --- | --- | --- | --- | --- |
| | Plasmid Name | Amount of plasmid (μg) | Plasmid Name | Amount of plasmid (μg) |
| 1 | pCMV-AcGFP1 | 2.5 | — | — |
| 2 | pCMVTAR-AcGFP1 | 2.5 | — | — |
| 3 | pCMVTAR-AcGFP1 | 2.5 | pCMV-Tat | 0.02 |
| 4 | pCMVTAR-AcGFP1 | 2.5 | pCMV-Tat | 0.1 |
| 5 | pCMVTAR-AcGFP1 | 2.5 | pCMV-Tat | 0.5 |
| 6 | pCMVTAR-AcGFP1 | 2.5 | pCMVTAR-Tat | 0.02 |
| 7 | pCMVTAR-AcGFP1 | 2.5 | pCMVTAR-Tat | 0.1 |
| 8 | pCMVTAR-AcGFP1 | 2.5 | pCMVTAR-Tat | 0.5 |
| 9 | — | — | — | — |

The cells after the introduction were cultured in a $CO_2$ incubator for one day, and then harvested. A part of the harvested cells were subjected to a flow cytometry and a remarkable enhancement of AcGFP1-expression similar to Example 2 was found. Of the remaining cells, $1 \times 10^6$ of cells were used to prepare cell lysates in the same way as Example 2. These lysates were subjected to SDS-polyacrylamide gel electrophoresis, and Western blotting was performed using anti-HIV-1 Tat antibody (manufactured by abcam) and anti-α-tubulin antibody (manufactured by Cell Signaling Technology, Inc.), the latter was used for an evaluation of the amount subjected to the electrophoresis between the samples. SuperSignal (registered trademark) West Femto Maximum Sensitivity Substrate (manufactured by Thermo Fisher Scientific Inc.) was used to detect the antibodies, and chemiluminescence detection device LuminoShot (registered trademark) 140 (manufactured by Takara Bio Inc.) was used to capture the detection. Each signal intensity was converted into numerical values, and (Tat signal intensity/α-Tubulin signal intensity) was calculated and used as corrected Tat signal intensities. FIG. 3 shows the results.

According to FIG. 3, it was shown that the expression amount of Tat was clearly improved by using pCMVTAR-Tat having the transcriptional activator-expression cassette of the present invention as a Tat expression plasmid, compared with pCMV-Tat. Accordingly, it was shown that the enhancement of AcGFP1-expression was due to the enhancement of Tat-expression.

Example 4: Enhancement of AcGFP1 Expression in Floating 293 Cells (1) Evaluation by AcGFP1 Fluorescence Intensity FreeStyle293 Expression system (manufactured by Life Technologies), which is a culture system of floating 293 cell, was used, and floating 293 cells were seeded at $2 \times 10^7$ cells/20 mL in a 125-mL flask and cultured according to the protocol attached to the kit. Then, AcGFP1 expression plasmids were introduced into the cells. Table 5 shows the type and the amount of the plasmids used under each test condition.

TABLE 5

| Test condition | AcGFP1 expression plasmid | | Tat expression plasmid | |
|---|---|---|---|---|
| | Plasmid Name | Amount of plasmid (μg) | Plasmid Name | Amount of plasmid (μg) |
| 1 | pCMV-AcGFP1 | 20 | — | — |
| 2 | pCMVTAR-AcGFP1 | 20 | — | — |
| 3 | pCMVTAR-AcGFP1 | 20 | pCMVTAR-Tat | 0.16 |
| 4 | pCMVTAR-AcGFP1 | 20 | pCMVTAR-Tat | 4 |
| 5 | — | — | — | — |

The cells after the introduction were cultured in a $CO_2$ incubator for two days. Then, the cultured cells were subjected to a flow cytometry to measure fluorescence by AcGFP1 expressed in the cell. Table 6 shows the mean fluorescence intensities of the cells in which the fluorescence was observed.

TABLE 6

| Test condition | Mean fluorescence intensity |
|---|---|
| 1 | 4,051 |
| 2 | 15,072 |
| 3 | 32,872 |
| 4 | 37,447 |
| 5 | 0 |

As a result, it was shown that, similar to the adherent 293T cells, AcGFP1 expression was markedly enhanced under the condition in which pCMVTAR-Tat and pCMVTAR-AcGFP1 were used (test conditions 3, 4) in the floating 293 cells.

Example 5: Construction of a Plasmid Having a Transcriptional Activator-Expression Cassette and a Target Product-Expression Cassette on the Same Molecule A plasmid in which an IRES sequence derived from picornavirus and a nucleic acid encoding Tat (SEQ ID NO: 1) were inserted on the downstream of the sequence encoding AcGFP1 of pCMVTAR-AcGFP1 plasmid was constructed, and named pCMVTAR-AcGFP1-IRES-Tat.

Example 6: Enhancement of AcGFP1 Expression by Tat-Expression pCMVTAR-AcGFP1-IRES-Tat constructed in Example 5 was used to evaluate an AcGFP1 expression-enhancing action in adherent 293T cells. The evaluation was performed in the same way as Example 2. However, the condition for seeding cells per well was $1.5 \times 10^5$ cells/1 mL. Table 7 shows the type and the amount of the plasmids used under each test condition.

TABLE 7

| | | AcGFP1 expression plasmid | |
|---|---|---|---|
| Test condition | Cell | Plasmid Name | Amount of plasmid (μg) |
| 1 | Adherent 293T cell | pCMV-AcGFP1 | 1 |
| 2 | | pCMVTAR-AcGFP1-IRES-Tat | 1 |
| 3 | | — | — |

The cells after the introduction were cultured in a $CO_2$ incubator for two days. Then, the cultured cells were subjected to a flow cytometry to measure fluorescence by AcGFP1 expressed in the cell. Table 8 shows the mean fluorescence intensities of the cells in which the fluorescence was observed.

TABLE 8

| Test condition | Mean fluorescence intensity |
|---|---|
| 1 | 4,363 |
| 2 | 29,459 |
| 3 | 0 |

As a result, it was shown that AcGFP1 expression was markedly enhanced under the condition in which pCMVTAR-AcGFP1-IRES-Tat was used (test condition 2). That is, the transcriptional activator-expression cassette of the present invention and the target product-expression cassette of the present invention enhance the expression amount of the target product even if they are contained in a single plasmid.

Example 7: Construction of a Secretory Protein G-CSF Expression Plasmid

Plasmids in which a nucleic acid encoding granulocyte colony-stimulating factor (G-CSF) was inserted instead of the nucleic acid encoding AcGFP1 in pCMV-AcGFP1, pCMVTAR-AcGFP1 and pCMVTAR-AcGFP-IRES-Tat were constructed, and named pCMV-G-CSF, pCMVTAR-G-CSF and pCMVTAR-G-CSF-IRES-Tat, respectively.

Example 8: Enhancement of G-CSF Expression by Tat-Expression

The G-CSF expression plasmids constructed in Example 7 were used to evaluate a G-CSF expression-enhancing action in adherent 293T cells and floating 293 cells. The introduction into the adherent 293T cells was performed in the same way as Example 2. However, the condition for seeding cells was 5×10$^5$ cells/2 mL. The introduction into the floating 293 cells was performed in the same way as Example 4. However, the condition for seeding cells was 4.5×10$^7$ cells/30 mL in a 125-mL flask. Table 9 shows the type and the amount of the plasmids used under each test condition.

TABLE 9

| Test condition | Cell | G-CSF expression plasmid | | Tat expression plasmid | |
|---|---|---|---|---|---|
| | | Plasmid Name | Amount of plasmid (μg) | Plasmid Name | Amount of plasmid (μg) |
| 1 | Adherent 293T cell | pCMV-G-CSF | 2 | — | — |
| 2 | | pCMVTAR-G-CSF | 2 | — | — |
| 3 | | pCMVTAR-G-CSF | 2 | pCMVTAR-Tat | 0.016 |
| 4 | | pCMVTAR-G-CSF | 2 | pCMVTAR-Tat | 0.4 |
| 5 | | pCMVTAR-G-CSF-IRES-Tat | 2 | — | — |
| 6 | | — | — | — | — |
| 7 | Floating 293 cell | pCMV-G-CSF | 30 | — | — |
| 8 | | pCMVTAR-G-CSF | 30 | — | — |
| 9 | | pCMVTAR-G-CSF | 30 | pCMVTAR-Tat | 0.24 |
| 10 | | pCMVTAR-G-CSF | 30 | pCMVTAR-Tat | 6 |
| 11 | | pCMVTAR-G-CSF-IRES-Tat | 30 | — | — |
| 12 | | — | — | — | — |

The cells after the introduction were cultured in a $CO_2$ incubator and the culture supernatant was sampled by 0.08 ml each on days 2, 5, and 7. The sampled culture supernatants were used for measuring the amount of G-CSF. The measurement was performed with Human G-CSF Assay Kit (manufactured by IBL Co., Ltd.) according to the protocol attached to the kit. Table 10 shows the results.

TABLE 10

| Test condition | Cell | Amount of G-CSF (μg/mL) | | |
|---|---|---|---|---|
| | | Day 2 | Day 5 | Day 7 |
| 1 | Adherent 293T cell | 0.7 | 2.0 | 2.1 |
| 2 | | 1.4 | 2.4 | 3.0 |
| 3 | | 2.7 | 6.3 | 7.1 |
| 4 | | 2.9 | 5.9 | 6.9 |
| 5 | | 3.2 | 6.1 | 7.3 |
| 6 | | 0 | 0 | 0 |
| 7 | Floating 293 cell | 1.2 | 2.9 | 2.3 |
| 8 | | 1.8 | 3.3 | 3.5 |
| 9 | | 4.0 | 7.7 | 8.8 |
| 10 | | 6.3 | 11.4 | 12.0 |
| 11 | | 4.5 | 7.8 | 8.4 |
| 12 | | 0 | 0 | 0 |

As a result, also regarding G-CSF which is a secretory protein, the significantly improvement of the expression amount was shown under the condition in which the expression cassette of the present invention using TAR and Tat was used (test conditions 3-5, 9-11).

Example 9: Construction of Anti-Human CD3 Antibody Expression Plasmid

Plasmids in which a nucleic acid encoding a heavy chain or a light chain of anti-human CD3 antibody was inserted instead of the nucleic acid encoding AcGFP1 of pCMVTAR-AcGFP1 were constructed, respectively, and named pCMVTAR-HC and pCMVTAR-LC, respectively.

Example 10

The anti-human CD3 antibody expression plasmids constructed in Example 9 were used to evaluate the enhancement of an anti-human CD3 antibody expression in adherent 293T cells and floating 293 cells. The introduction into the adherent 293T cells was performed in the same way as Example 2 and the introduction into the floating 293 cells was performed in the same way as Example 8. Table 11 shows the type and the amount of the plasmids used under each test condition.

TABLE 11

| Test condition | Cell | Anti-human CD3 antibody expression plasmid | | Tat expression plasmid | |
|---|---|---|---|---|---|
| | | Plasmid Name | Amount of plasmid (μg) | Plasmid Name | Amount of plasmid (μg) |
| 1 | Adherent 293T cell | pCMVTAR-HC pCMVTAR-LC | 0.5 each | — | — |
| 2 | | pCMVTAR-HC pCMVTAR-LC | 0.5 each | pCMVTAR-Tat | 0.008 |
| 3 | | — | — | — | — |
| 4 | Floating 293 cell | pCMVTAR-HC pCMVTAR-LC | 15 each | — | — |
| 5 | | pCMVTAR-HC pCMVTAR-LC | 15 each | pCMVTAR-Tat | 0.24 |
| 6 | | — | — | — | — |

The cells after the introduction were cultured in a $CO_2$ incubator and the culture supernatant was sampled by 0.04 ml each on days 2, 5, and 7. The sampled culture supernatants were used for measuring the production amount of anti-human CD3 antibody. The measurement was performed with Mouse IgG EIA Kit (manufactured by Takara Bio Inc.) according to the protocol attached to the kit. Table 12 shows the results.

TABLE 12

| Test condition | Cell | Production amount of anti-CD3 antibody (μg/mL) | | |
|---|---|---|---|---|
| | | Day 2 | Day 5 | Day 7 |
| 1 | Adherent 293T cell | 4.4 | 11.7 | 14.3 |
| 2 | | 6.0 | 21.5 | 28.2 |
| 3 | | 0 | 0 | 0 |
| 4 | Floating 293 cell | 3.6 | 5.6 | 6.5 |
| 5 | | 4.9 | 10.7 | 14.7 |
| 6 | | 0 | 0 | 0 |

As a result, also regarding anti-CD3 antibody, the significantly improved expression amount was shown under the condition in which the expression cassette of the present invention using TAR and Tat was used (test conditions 2, 5).

INDUSTRIAL APPLICABILITY

The present invention is very useful for basic studies or clinical applications in the fields of not only protein engineering and molecular genetics but also immunoengineering, gene therapy, and pharmaceutical production.

Sequence Listing Free Text
    SEQ ID NO: 1: Tat coding sequence
    SEQ ID NO: 2: Nucleic acid sequence corresponding to TAR
    SEQ ID NO: 3: Nucleic acid sequence including sequence corresponding to TAR

The invention claimed is:

1. A nucleic acid construct comprising the following (i) to (iv):

(i) an expression regulatory region having a promoter and a transcriptional activator-binding region sequence;

(ii) a nucleic acid encoding a transcriptional activator which is capable of binding to the expression regulatory region, wherein the nucleic acid is operably linked to the first expression regulatory region, (iii) a) a nucleic acid for expressing a target product that is operably linked to the second expression regulatory region or b) a site into which a nucleic acid for expressing a target product is insertable so that the nucleic acid is operably linked to the second expression regulatory region; and (iv) an internal ribosome entry site (IRES) sequence or a sequence encoding 2A peptide that is inserted between (ii) and (iii);

```
SEQUENCE LISTING

<160> NUMBER OF SEQ ID NOS: 3

<210> SEQ ID NO 1
<211> LENGTH: 261
<212> TYPE: DNA
<213> ORGANISM: Artificial Sequence
<220> FEATURE:
<223> OTHER INFORMATION: Tat coding sequence

<400> SEQUENCE: 1
atggagccag tagatcctag actagagccc tggaagcatc caggaagtca gcctaaaact      60
gcttgtacca attgctattg taaaaagtgt tgctttcatt gccaagtttg tttcatgaca     120
aaagccttag gcatctccta tggcaggaag aagcggagac agcgacgaag agctcatcag     180
aacagtcaga ctcatcaagc ttctctatca aagcaaccca cctcccaatc ccgaggggac     240
ccgacaggcc cgaaggaata g                                              261

<210> SEQ ID NO 2
<211> LENGTH: 59
<212> TYPE: DNA
<213> ORGANISM: Artificial Sequence
<220> FEATURE:
<223> OTHER INFORMATION: Nucleic acid sequence corresponding to TAR

<400> SEQUENCE: 2
gggtctctct ggttagacca gatctgagcc tgggagctct ctggctaact agggaaccc       59

<210> SEQ ID NO 3
<211> LENGTH: 213
<212> TYPE: DNA
<213> ORGANISM: Artificial Sequence
<220> FEATURE:
<223> OTHER INFORMATION: Nucleic acid sequence including sequence
      corresponding to TAR

<400> SEQUENCE: 3
gtacttcaag aactgctgat atcgagcttg ctacaaggga ctttccgctg gggactttcc      60
agggaggcgt ggcctgggcg ggactgggga gtggcgagcc ctcagatcct gcatataagc     120
agctgctttt tgcctgtact gggtctctct ggttagacca gatctgagcc tgggagctct     180
ctggctaact agggaaccca ctgcttaagc ctc                                 213
``` wherein the promoter is selected from CMV promoter, SV40 promoter, EF-1α promoter, CAG promoter, and PGK promoter, wherein the transcriptional activator is Tat of immunodeficiency virus or a functionally homologous variant thereof, wherein the functionally homologous variant consists of an amino acid sequence having 95% or more identity to the amino acid sequence encoded by the base sequence of SEQ ID NO: 1, and wherein the transcriptional activator-binding region is a trans-activation-responsive region of immunodeficiency virus or a functionally homologous sequence thereof, wherein the functionally homologous sequence has 95% or more homology to the base sequence of SEQ ID NO: 2.

2. A method for producing a target product in a mammalian cell comprising the following steps (a) to (d):
(a) introducing into a cell the nucleic acid construct of claim 1;
(b) culturing the cell obtained in the step (a);
(c) expressing the target product by the step (b); and
(d) obtaining the expressed target product.

3. A method for producing a cell expressing a target product in vitro, comprising a step of introducing into a mammalian cell the nucleic acid construct of claim 1.

4. A kit comprising the nucleic acid construct of claim 1.

5. A set of nucleic acid constructs, comprising the following (1) and (2):
(1) a first nucleic acid construct comprising a first expression cassette comprising:
(i) a first expression regulatory region having a first promoter and a first transcriptional activator-binding region sequence; and
(ii) a nucleic acid encoding a transcriptional activator which is capable of binding to the first expression regulatory region, wherein the nucleic acid is operably linked to the first expression regulatory region, and
(2) a second nucleic acid construct comprising a second expression cassette comprising:
(i) a second expression regulatory region having a second promoter and a second transcriptional activator-binding region sequence; and
(ii) a) a nucleic acid for expressing a target product that is operably linked to the second expression regulatory region or b) a site into which a nucleic acid for expressing a target product is insertable so that the nucleic acid is operably linked to the second expression regulatory region, wherein the first and second promoters are each independently selected from the group consisting of CMV promoter, SV40 promoter, EF-1α promoter, CAG promoter, and PGK promoter, wherein the first and second promoters are the same or different, wherein the first and second expression regulatory region are the same or different, wherein the transcriptional activator is Tat of immunodeficiency virus or a functionally homologous variant thereof, wherein the functionally homologous variant consists of an amino acid sequence having 95% or more identity to the amino acid sequence encoded by the base sequence of SEQ ID NO: 1, and wherein the first and second transcriptional activator-binding regions are each independently a trans-activation-responsive region of immunodeficiency virus or a functionally homologous sequence thereof, wherein the functionally homologous sequence has 95% or more homology to the base sequence of SEQ ID NO: 2, wherein the first and second transcriptional activator-binding regions are the same or different, and wherein the first nucleic acid construct and the second nucleic acid construct do not comprise an origin of replication wherein the origin of replication allows for replication in an animal cell.

6. A method for producing a target product in a mammalian cell comprising the following steps (a) to (d):
(a) introducing into a cell the set of nucleic acid constructs of claim 5;
(b) culturing the cell obtained in the step (a);
(c) expressing the target product by the step (b); and
(d) obtaining the expressed target product.

7. A method for producing a cell expressing a target product in vitro, comprising a step of introducing into a mammalian cell the set of nucleic acid constructs of claim 5.

8. A kit comprising the set of nucleic acid constructs of claim 5.

* * * * *